(12) United States Patent
Perfler

(10) Patent No.: US 10,980,597 B2
(45) Date of Patent: Apr. 20, 2021

(54) ABLATION CATHETER AND ABLATION APPARATUS

(71) Applicant: Electrophysiology Frontiers S.P.A., Turin (IT)

(72) Inventor: Enrico Perfler, Pavia (IT)

(73) Assignee: ElectroPhysiology Frontiers S.p.A., Turin (IT)

( * ) Notice: Subject to any disclaimer, the term of this patent is extended or adjusted under 35 U.S.C. 154(b) by 98 days.

(21) Appl. No.: 15/127,464

(22) PCT Filed: Mar. 18, 2015

(86) PCT No.: PCT/IB2015/051998
§ 371 (c)(1),
(2) Date: Sep. 20, 2016

(87) PCT Pub. No.: WO2015/140741
PCT Pub. Date: Sep. 24, 2015

(65) Prior Publication Data
US 2017/0151014 A1  Jun. 1, 2017

(30) Foreign Application Priority Data
Mar. 20, 2014 (IT) .......................... MI2014A000467

(51) Int. Cl.
*A61B 18/14* (2006.01)
*A61B 18/12* (2006.01)
*A61B 18/00* (2006.01)

(52) U.S. Cl.
CPC ...... *A61B 18/1492* (2013.01); *A61B 18/1206* (2013.01); *A61B 2018/0016* (2013.01); *A61B 2018/00214* (2013.01); *A61B 2018/00267* (2013.01); *A61B 2018/00273* (2013.01); *A61B 2018/00279* (2013.01);
(Continued)

(58) Field of Classification Search
CPC .. A61B 2018/0016; A61B 2018/00214; A61B 2018/00267; A61B 2018/00273; A61B 2018/00279; A61B 2018/00285; A61B 2018/00375; A61B 2018/00577; A61B 2018/00654; A61B 2018/00839; A61B 2018/1273; A61B 2018/1405; A61B 2018/1467; A61B 2018/1475; A61B 18/1492; A61B 18/1206
See application file for complete search history.

(56) References Cited

U.S. PATENT DOCUMENTS 5,471,982 A    12/1995  Edwards et al.
5,772,590 A *   6/1998  Webster, Jr. .......... A61B 5/0422
                                                    600/374
(Continued)

OTHER PUBLICATIONS

Fischer, Olivier, "International Preliminary Report on Patentability for International Application No. PCT/IB2015/051998," European Patent Office, dated Jun. 8, 2016.

*Primary Examiner* — Thomas A Giuliani
*Assistant Examiner* — Christine A Dedoulis
(74) *Attorney, Agent, or Firm* — Nixon & Vandernye P.C.

(57) ABSTRACT

An ablation catheter equipped with ablation petals having electrodes that are continuous over an outer circumferential portion of the ablation petals. The ablation catheter can be moved from a rest position, where the petals are housed in an external tubular body, to an operating position, where the petals protrude from the external tubular body.

18 Claims, 10 Drawing Sheets

(52) U.S. Cl.
CPC .............. *A61B 2018/00285* (2013.01); *A61B 2018/00375* (2013.01); *A61B 2018/00577* (2013.01); *A61B 2018/00654* (2013.01); *A61B 2018/00839* (2013.01); *A61B 2018/1273* (2013.01); *A61B 2018/1405* (2013.01); *A61B 2018/1467* (2013.01); *A61B 2018/1475* (2013.01)

(56) References Cited

U.S. PATENT DOCUMENTS

| | | | |
|---|---|---|---|
| 6,163,716 A * | 12/2000 | Edwards | A61B 5/0422 128/898 |
| 6,315,778 B1 | 11/2001 | Gambale et al. | |
| 2001/0021867 A1 | 9/2001 | Kordis et al. | |
| 2005/0171536 A1 | 8/2005 | Phan et al. | |
| 2006/0021867 A1 | 4/2006 | Maguire et al. | |
| 2007/0219546 A1 | 9/2007 | Mody et al. | |
| 2009/0093802 A1* | 4/2009 | Kulesa | A61B 18/1492 606/33 |
| 2009/0105700 A1* | 4/2009 | Anderson | A61B 18/1492 606/27 |
| 2011/0028826 A1* | 2/2011 | Kim | A61B 5/0422 600/407 |
| 2012/0010608 A1 | 1/2012 | Malecki et al. | |
| 2014/0052208 A1* | 2/2014 | Ransbury | A61N 1/3621 607/14 |
| 2014/0358135 A1* | 12/2014 | Sambelashvili | A61B 18/02 606/21 |
| 2014/0358143 A1* | 12/2014 | Novichenok | A61B 18/1492 606/49 |

\* cited by examiner

B-B

C-C

ABLATION CATHETER AND ABLATION APPARATUS

TECHNICAL FIELD

The present invention relates to the general field of catheters and ablation apparatuses for human tissue ablation or, more generally, for animals.

STATE OF THE ART

Various type of ablation catheters are known in the state of the art.

In general, the term "ablation" refers, in the medical field, to the treatment of a tissue suitable for removing a surface part of the same tissue or necrotizing it and/or causing a cicatrization of the same.

The ablation referred to in this invention is specifically destined for interrupting the electric continuity of the tissue in correspondence with the zone treated by ablation.

In this sense, ablation can take place with a series of treatments, for example by means of an electric current, by heat, cryogenics, radiofrequencies or other forms of treatment.

A first example of a radiofrequency ablation catheter is that capable of effecting focal ablations: in fact, it has an actual ablation tip in correspondence with its free end.

In the treatment, the catheter is inserted by means of percutaneous access and is brought to the area to be ablated.

The surgeon then activates the ablation tip and effects the ablation of the tissues by means of a continuous approach/distancing movement of the ablation tip from the tissue, necessary for not maintaining an excessively lengthy contact of the tip with the tissue, with consequent damage that can be critical.

The ablated area is therefore defined by the combination of ablated punctiform zones.

This operation is particularly delicate as an excessively prolonged contact of the tip with the tissue can lead to serious injury to the latter.

Let us consider, for example, the ablation of the antrum of the pulmonary veins in the case of atrial fibrillation: the antrum of the veins to be ablated is situated in correspondence with the conjunction of the veins with the heart; an excessively prolonged contact of the ablation tip with the tissue could lead to a piercing of the wall of the heart and, if not immediately treated surgically, could have fatal consequences for the patient.

The ablation manoeuvring itself, on the other hand, must also be sufficiently prolonged for ensuring that the ablation is effective and does not have to be repeated.

This situation, already complex, is made even more so due to the fact that this type of ablation generates substantially punctiform ablated areas, and consequently the treatment must be repeated numerous times, in order to join these punctiform areas until they form a substantially continuous ablation line to interrupt the electric continuity of the tissue and isolate the atrium from the venous electric disturbances. The intervention therefore has relatively lengthy times which require a prolonged sedation of the patient.

Furthermore, in order to improve the precision of the treatment, the radiofrequency ablation catheter described above requires a second, separate, catheter, i.e. a mapping catheter, which obtains information on the position and effectiveness of the treatment of the single areas to be treated.

This implies having to introduce and manoeuvre two separate catheters, with relatively high encumbrance, costs and overall procedural difficulties.

Another type of known catheter, specifically suitable for the ablation of the antrum of the pulmonary veins (for the treatment of atrial fibrillation) is described in international patent application PCT/EP2012/056626.

This catheter was created for at least partly solving the problems indicated above.

It comprises a positioning head and an ablation head and a telescopic tubular body provided with an external tubular body, an internal tubular body, concentric with each other, and a rod-like guiding element at least partly housed in the internal tubular body with a free end protruding from the internal tubular body.

The positioning head is situated in the proximity of the free end of the rod-like guiding element, whereas the ablation head is positioned close to the positioning head, in a position far from the free end, i.e. on the opposite side of the latter with respect to the positioning head.

In short, the positioning head and the ablation head can be inflated by suitable fluids so as to pass from a rest position in which they are deflated and not expanded, to an operating condition in which they are inflated and expanded.

Although this catheter represents a considerable step forward with respect to those having an "ablation tip" described above, it still has various drawbacks.

A first drawback is linked to the fact that it has a certain encumbrance even when in a rest condition: it should in fact be remembered that catheters are inserted in the patient's veins and are brought through these to the treatment zones, which can often be distant from the inlet point (for example in the treatment of atrial fibrillation, the catheter is inserted in the femoral vein and brought up to the heart).

In this sense, it is evident that it is extremely important to limit the encumbrance of the catheter in order to facilitate its passage in the veins of the patient undergoing treatment.

Another drawback is linked to the fact that the ablation head of the catheter described therein is a torus, which, once expanded, has well-defined dimensions: in a functioning condition, its dimensions cannot therefore be varied.

This implies knowing the exact dimensions of the area to be treated, in order to be able to select the correct catheter, i.e. having a torus which, in expanded conditions, has dimensions coherent with those of the area to be treated.

A further drawback, again linked to the dimensions of the torus described above, lies in the fact that the same catheter cannot be used for different applications, for example, applications in which the dimensions required by the ablation head differ significantly (for example for veins having a different ostium in the same patient).

Yet another drawback relates to the fact that some ablated areas sometimes require a second ablation treatment in order to be effective.

An example is the case of the ablation of the antrum of a vein: the ablation line in which the tissue is altered by the treatment is substantially a circumference; if an arc of the same is not treated sufficiently, the surgeon must proceed with a new treatment.

The intrinsic characteristics of the catheter described above, however, imply that a new treatment presumably also involves areas of the circumference that have already been sufficiently treated, therefore exposing the tissue to potential injury.

Another known ablation catheter is that described in US2013/0103027. In this case, there are two separate heads in the distal portion, an ablation head and a positioning head.

The ablation head has angled thread-like supports on which discrete ablation electrodes (punctiforms) are assembled.

Yet another ablation catheter is that described in US2005171536: also in this case, the ablation head has electrodes assembled on a supporting structure.

The same can be said, in short, for the catheter described in U.S. Pat. No. 6,893,438.

Although these types of embodiments are capable of overcoming some of the drawbacks described above with respect to the more traditional catheters (with a tip and inflatable), they are, however, relatively complex to construct, they require specific conductors for feeding the electrodes and occupy considerable space.

Furthermore, it should be pointed out that during the ablation operation in catheters with discrete electrodes, the risk of the formation of blood clots is relatively high, due to the fact that, on the whole, it is difficult to make the electrodes of each wire of the supporting structure adhere perfectly to the surface of tissue to be ablated.

Another problem encountered with the "multi-electrode" catheters described above is due to the discrete arrangement of the electrodes: said electrodes, which can be activated with a monopolar or bipolar radiofrequency supply, ablate the tissue surrounding the pulmonary veins, leaving however gaps between one ablation point and another. In order to fill these gaps, repeated applications of the same catheter or even the introduction of a focal catheter and a mapping catheter are very frequently required for identifying and completing the ablation in areas not completely treated, with a consequent increase in the procedural risk for the patient and an increase in the times and intervention costs.

On the whole, radiofrequency ablation is more difficult to control, due to eddy currents that can be generated in the conductors along the catheter, from the generator (external) to the ablation head, which can make it difficult to accurately control the quantity of energy supplied.

OBJECTIVES OF THE INVENTION

A first objective of the present invention is to overcome the drawbacks of the known art.

A second objective of the invention is to provide a catheter for the ablation of tissues which has the minimum possible dimensions and at the same time has an ablation profile which is as ample and uniform as possible.

A further objective is to also enable ablations to be effected of only part of the tissue surrounding the ablation head, without requiring that other parts already treated correctly be subjected to new treatment.

Yet another objective of the invention is to provide a catheter for the ablation of tissues which is capable of shortening the time of the procedure, thus reducing the time in which the patient is sedated.

An additional objective is to provide an ablation catheter which is safer to use, also in the case of moving tissue walls, and which avoids injury to or piercing of the walls.

A further objective of the invention is to provide an ablation catheter which, when in use, has a reduced formation of clots.

Yet another objective of the invention is to provide an ablation catheter which, when in use, has a relatively simple regulation of the energy supplied.

Another objective of the invention is to provide an ablation catheter which is capable of providing the surgeon with information relating to the state of treatment of the tissue.

A first object of the invention therefore relates to an ablation catheter and a second object of the invention relates to an ablation apparatus comprising said catheter according to the enclosed independent claims.

The idea at the basis of the invention is to produce a catheter for the ablation of tissues comprising:

a telescopic tubular body in turn comprising an external tubular body and an internal tubular body, concentric with each other, and a rod-like guiding element at least partly housed in the internal tubular body with at least one free end protruding from the internal tubular body in correspondence with a distal end of the telescopic body;

a positioning head and an ablation head in correspondence with the distal end of the telescopic body, the positioning head being situated in the proximity of the free end of the rod-like guide, and the ablation head in the proximity of the positioning head, in a remote position with respect to the free end;

a control handpiece at a proximal end of the telescopic body coupled with the guiding element, the ablation head, the positioning head and the telescopic tubular body; the ablation head comprises at least two ablation elements or petals that can be moved from a rest position in which they are housed in the external tubular body and an operating position in which they protrude from the external tubular body like a petal;

characteristically, according to the invention, each of the ablation elements or petals comprises:

a continuous ablation electrode which extends without interruption over a circumferential peripheral portion of each petal, substantially along an arc of circumference having a longitudinal axis of the rod-like guiding element as its centre two side portions of the petal, each connected to an end of the ablation electrode, in correspondence with a curved section the side portions and the ablation electrode being integral with each other, formed by means of the same folded metallic conductor each ablation petal being separate and distinct from another ablation petal of the ablation head, all the ablation petals of the ablation head being separately connected to a distinct electric energy generator to cause a radiofrequency ablation in a powered ablation electrode condition.

In this way, the drawbacks indicated above are brilliantly overcome.

The ablation petals can in fact remain in rest position during the insertion and positioning of the catheter, until it has reached the position in which the treatment is to be effected: in this position, they are contained inside the external tubular element of the catheter and do not have any encumbrances or protrusions which could complicate the positioning manoeuvre and passage in the veins.

The reduced dimensions of the catheter, obtained through the advantageous expedients of the invention, therefore allow the catheter to be easily inserted and positioned.

In this respect, it should be pointed out that the fact that the side portions and the ablation electrode are integral with each other, formed by the same folded metallic conductor, allows a considerable reduction in the encumbrance and, at the same time, an optimum positioning which allows possible clots to be reduced: the intrinsic elasticity of the wire (or thin lamina) of which it is formed—and all the same for the whole petal—allows it to be positioned in optimum contact with the tissue to be subjected to ablation treatment, with the result that it is treated uniformly.

The Applicant has discovered that these advantages can be obtained when the petals are of Nitinol, produced with a single wire having a circular section with a diameter D and with the following ratio between the diameter D and the length L of the active part (circumferential part of the petal, i.e. electrode)

D/L ranging from 0.015 to 0.025, preferably equal to about 0.02.

This particular ratio linked to the material with which the petal is produced (Nitinol) ensures that optimal electric characteristics are obtained together with an optimum adhesion of the petal on the surface to be treated, so that it is possible to obtain perfectly straight lesions, without necrotized areas.

With a length L ranging from 10 to 25 mm, the relative optimum diameter preferably ranges from 0.20 mm to 0.50 mm, preferably 0.30 mm.

At the same time, the presence of continuous, non-discretized ablation electrodes, allows ablation sections having a much larger extension than those relating to catheters with an ablation tip, to be produced, thus reducing the treatment time during which the patient must be sedated.

Furthermore, with respect to structures in which the electrode is discrete and applied to a supporting structure, it can be noted that in this case, it is the same structure, conductor, that acts as electrode: the latter is therefore uniformly "distributed" so as to extend over the whole circumferential portion of the petal without interruptions.

According to a particularly advantageous characteristic, the ablation elements, or at least the relative segments, can be selectively activated, as each is connected to its own specific generator, part of the ablation apparatus which also comprises the same catheter of the invention: in this way, the surgeon can advantageously choose which and how many of these to activate for repeating the treatment, which can therefore correspond solely to the areas that have not been sufficiently treated, avoiding re-treating areas of tissue that have already been treated correctly or areas at risk for the patient.

In order to allow an optimum control of the energy supplied, according to an independent aspect of the invention, additional conductors are envisaged, which are useful for eliminating eddy currents that may be generated.

This feature can be advantageously combined with those of the catheter described herein, thus providing an extremely precise ablation catheter in the treatment.

In particular, but not exclusively, the ablation catheter of the invention is advantageously suitable for the ablation of the antrum of pulmonary veins for limiting or eliminating the atrial fibrillation phenomenon, thanks to the interruption in the electric currents induced by the veins themselves.

Details on this type of treatment for atrial fibrillation, its effectiveness and approach, can be found in scientific literature and consequently no further mention will be made thereof in the present description.

Other unlimited uses of the catheter of the invention can, for example, be for the ablation of renal arteries, as a cure for high blood pressure.

Also in this case, no medical details are provided on the treatment as these can be found in scientific literature.

Other optional advantageous features of the invention are contained in the enclosed claims, which should be considered as being an integral part of the present description.

BRIEF DESCRIPTION OF THE DRAWINGS

The invention is described hereunder with reference to non-limiting examples, provided for illustrative and non-limiting purposes in the enclosed drawings. These drawings illustrate different aspects and embodiments of the present invention and, when appropriate, reference numbers illustrating structures, components, materials and/or similar elements in different figures are indicated with similar reference numbers.

DETAILED DESCRIPTION OF THE INVENTION

Figure 1:
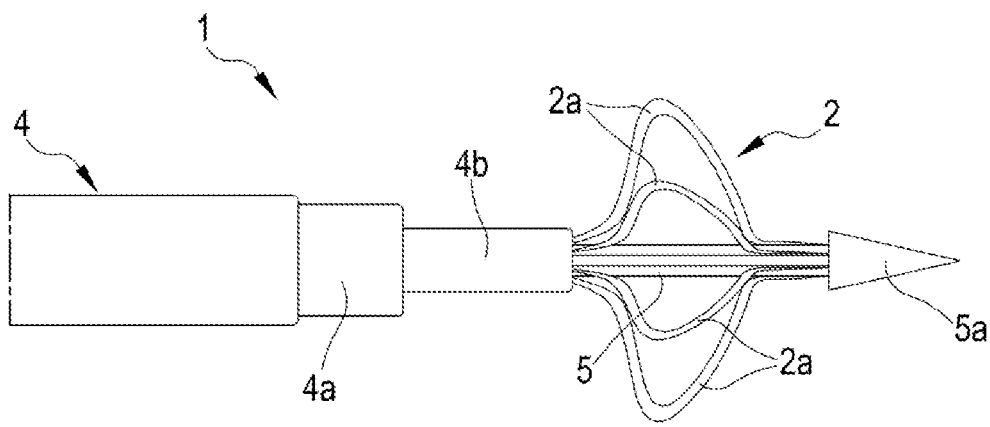
FIG. 1 illustrates a side view of the distal end of the catheter of the invention in a positioning condition.

Whereas the invention can undergo various modifications and alternative constructions, some relative illustrative embodiments are shown in the drawings and are described hereunder in detail.

It should be understood, however, that there is no intention of limiting the invention to the specific embodiment illustrated but, on the contrary, the invention intends to cover all the modifications, alternative constructions, and equivalents that fall within the scope of the invention as defined in the claims.

The use of "for example", "etc.", "or" indicates non-exclusive alternatives, without limitation, unless otherwise specified. The use of "comprises" means "comprises, but not limited to" unless otherwise specified.

With reference to the enclosed figures, these show an illustrative but non-limiting embodiment of the catheter of the invention, indicated as a whole with reference 1.

The catheter 1 comprises a positioning head 2 and an ablation head 3, which will be described in further detail hereunder.

The catheter 1 also comprises a handpiece in a proximal position, i.e. the control portion that is located outside and can be used for the operator for controlling the action of the catheter itself.

The control handpiece is positioned at a proximal end of the telescopic body 4 and is operatively connected to the guiding element 5, the ablation head 3, the positioning head 2,2",2"',2°,2*,2^ and the telescopic tubular body 4; said "operative connection" can be actuated in numerous ways, all known to skilled persons in the field, for example by means of control levers directly or indirectly connected to the above-mentioned parts; consequently no further mention will be made in this respect.

The form of the handpiece is of no particular interest for the present invention, as it is produced analogously to those known in the art; consequently no further detail is provided herein with respect to the handpiece.

The catheter 1 comprises a telescopic tubular body 4 in turn comprising: an outer tubular body 4a, an inner tubular body 4b, concentric with respect to each other.

A sheath 4c, also eccentric with respect to the tubular bodies 4a, 4b, is also envisaged for covering the outer tubular body.

The tubular bodies 4a and 4b are preferably cylindrical, even if, in general, they can be oval or polygonal (with rounded corners).

The catheter 1 also comprises a rod-like guiding element 5 partly housed in the inner tubular body 4b with a free end 5a which protrudes from the inner tubular body 4b.

The rod-like guiding element 5 is used by the surgeon for guiding the movement of the catheter 1 when inserting it into the patient's veins; this guiding element is per sé of the known type and no further mention will be made thereof.

Figure 2:
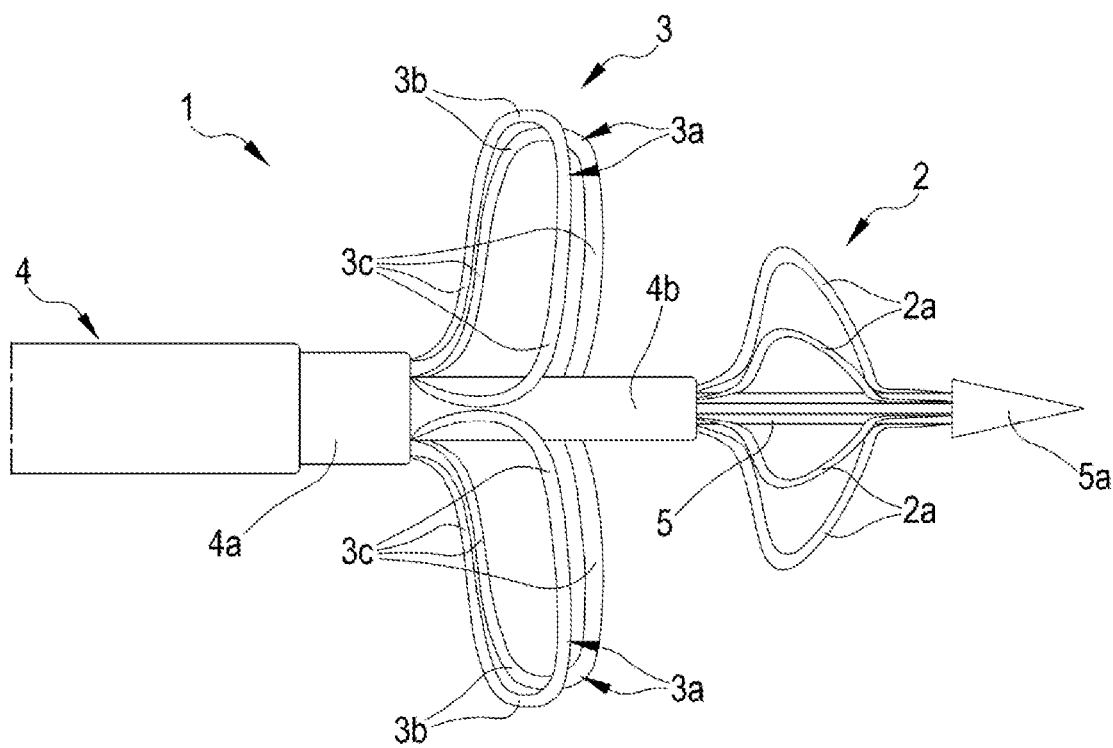
FIG. 2 illustrates a side view of the end of the catheter of FIG. 1 in a functioning condition.
Figure 11:
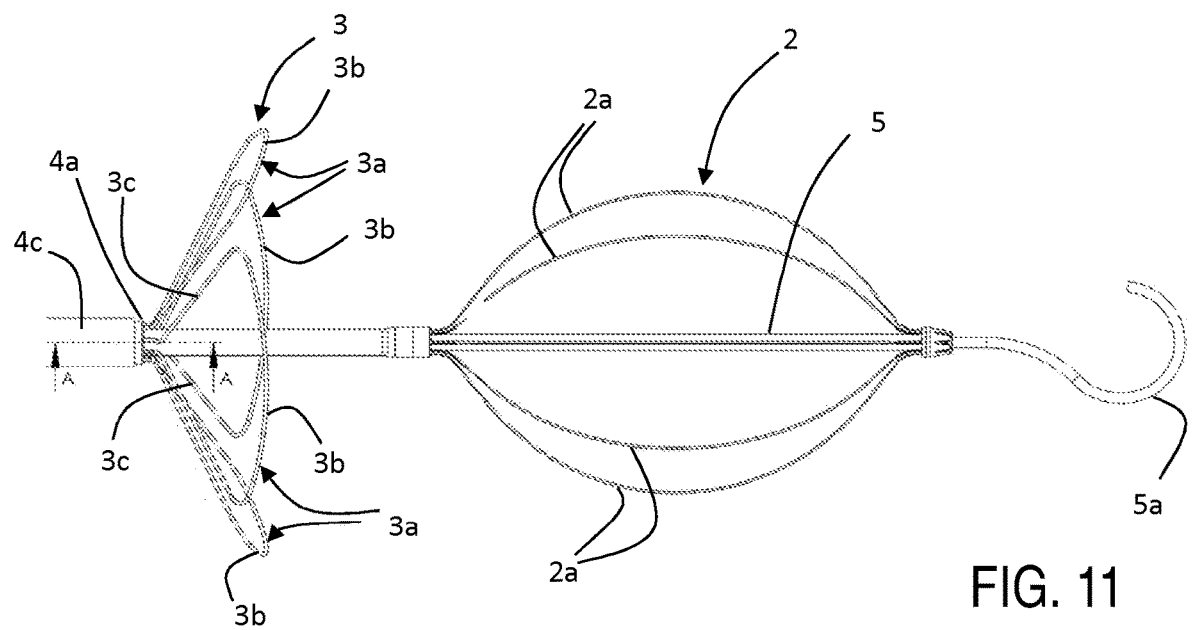
FIGS. 11 and 12 illustrate a preferred embodiment of the catheter of the invention, in a side and perspective view.
Figure 12:
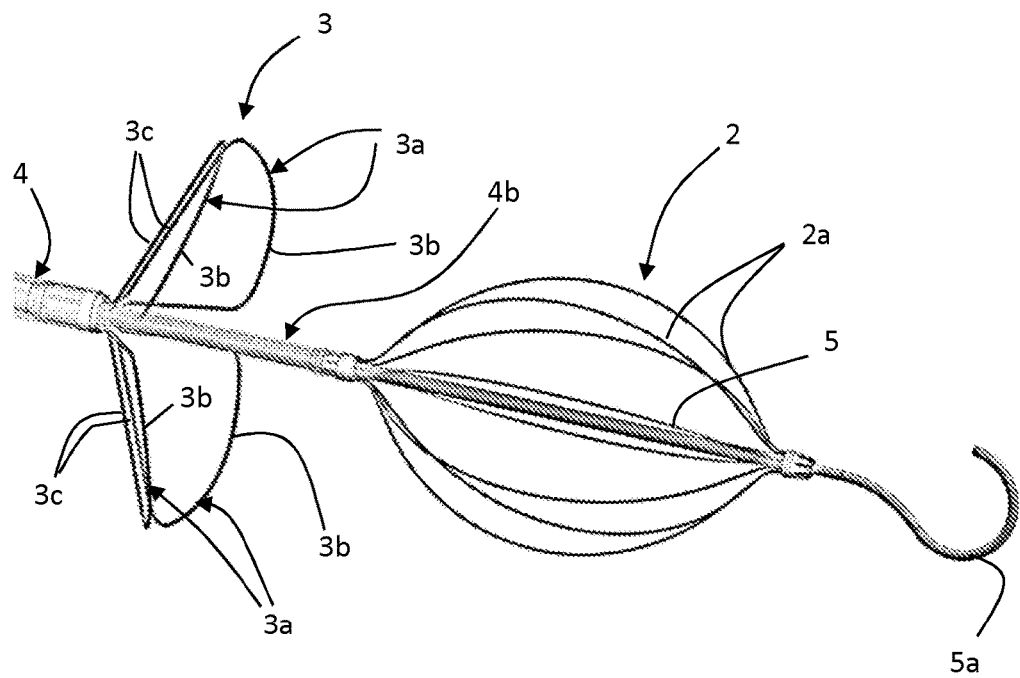
Figure 13:
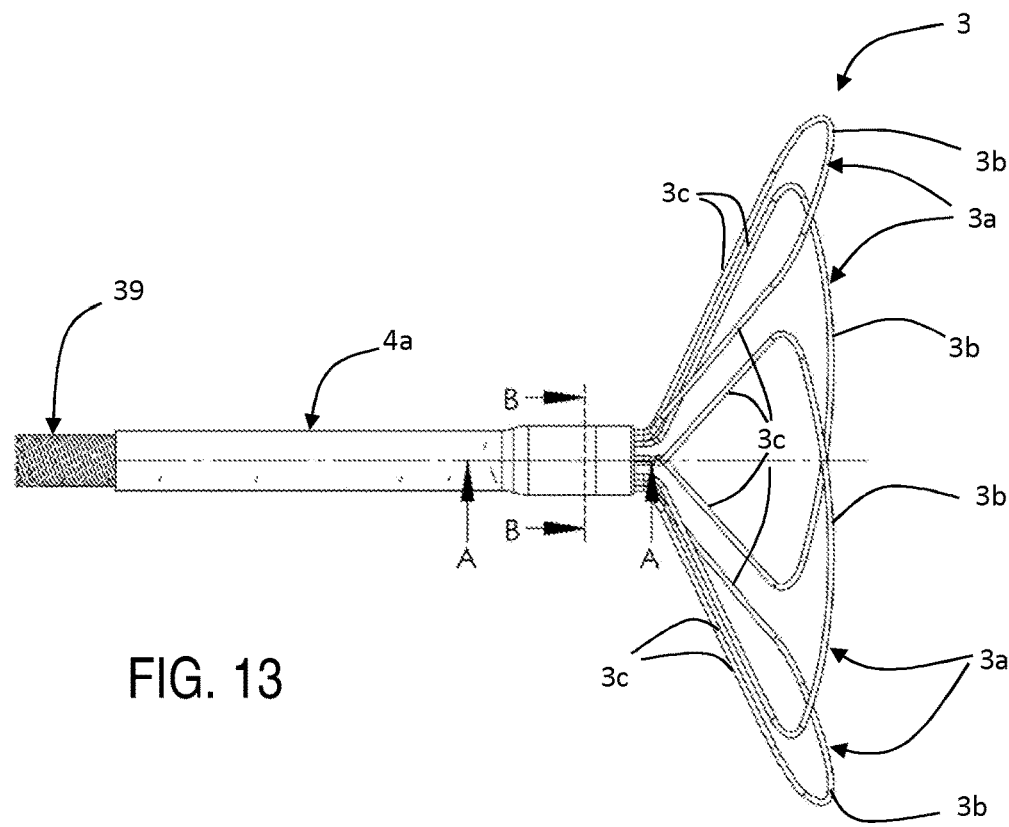
FIGS. 13 and 14 illustrate the ablation petals of the catheter of FIGS. 11, 12, in a side and perspective view.
Figure 14:
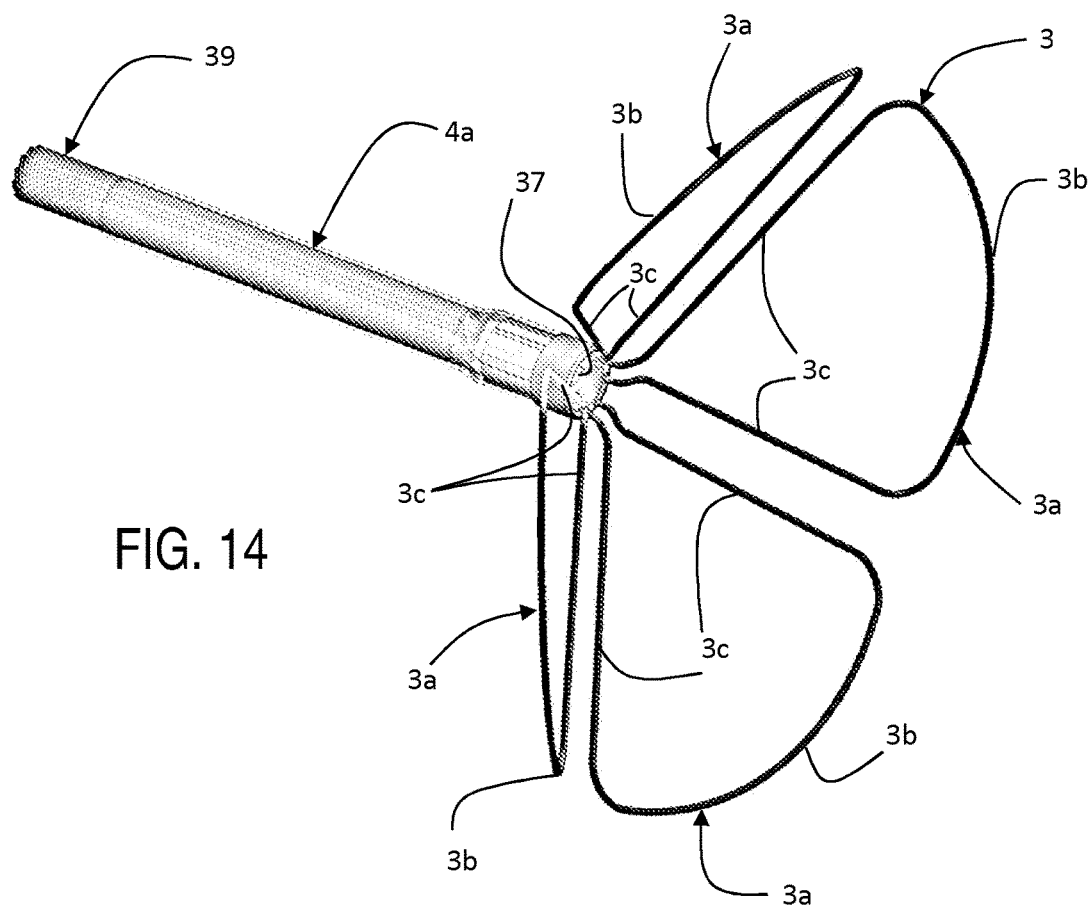
Figure 15:
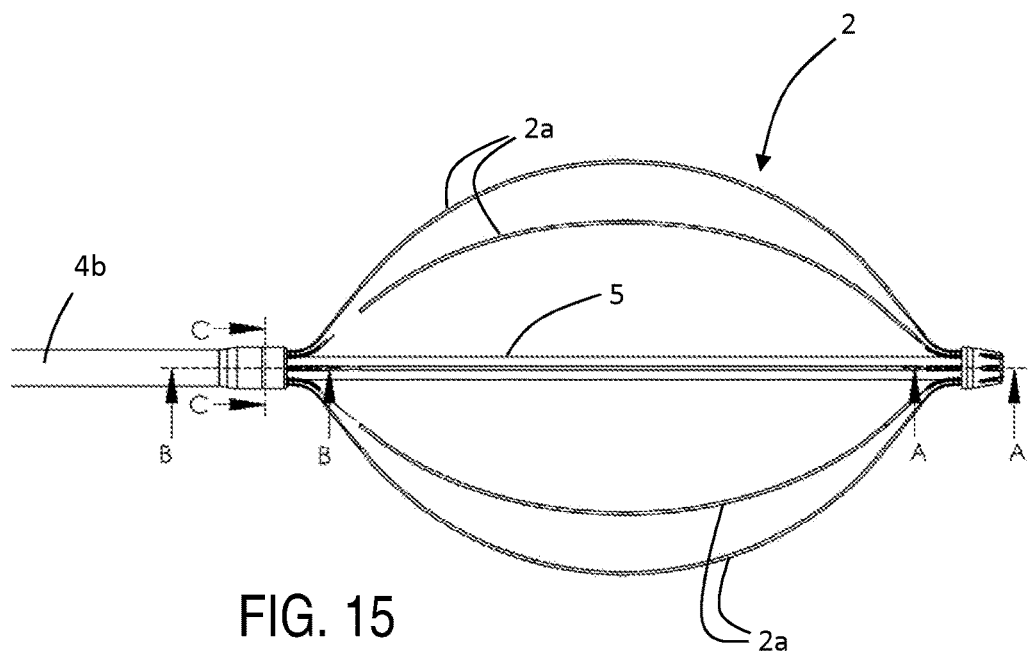
FIGS. 15 and 16 illustrate the positioning head of the catheter of FIGS. 11, 12, in a side and perspective view.
Figure 16:
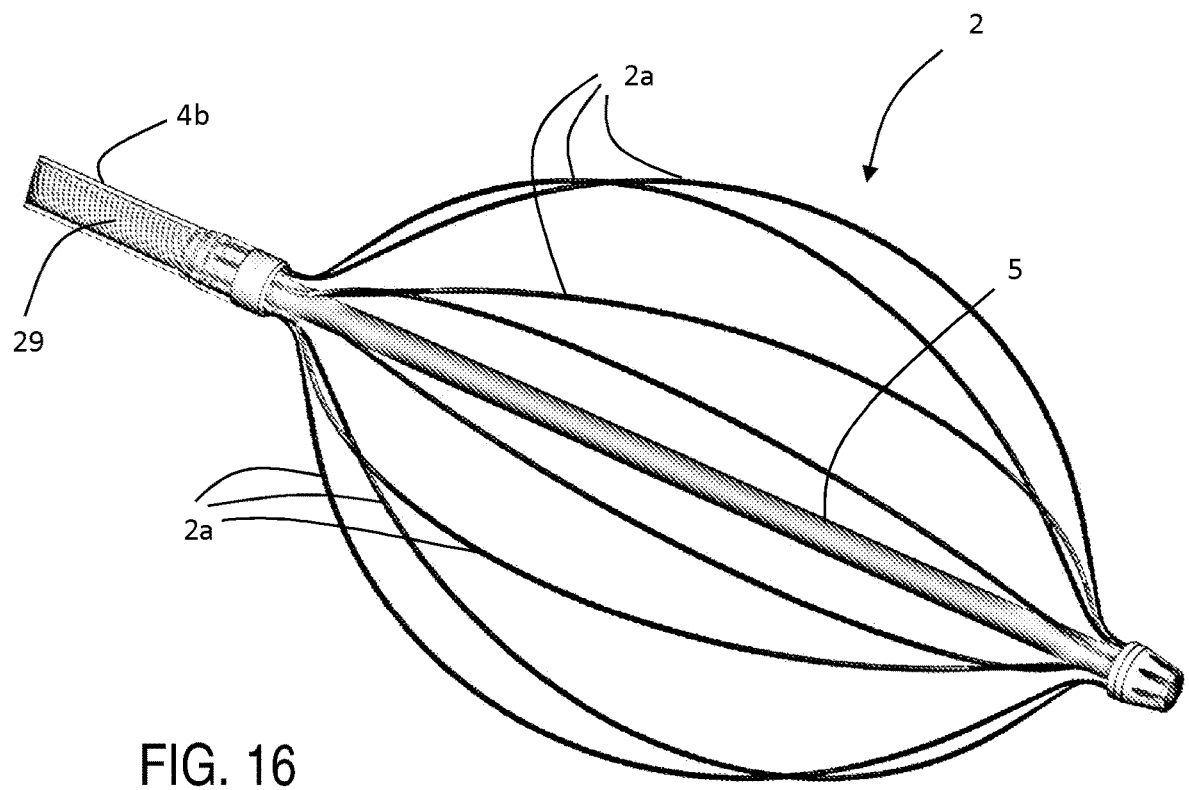

As can be seen in the figures, the positioning head 2 is situated in the proximity of the free end 5a of the rod-like guide 5, whereas the ablation head 3 is situated in the proximity of the positioning head 2, but in a remote position with respect to the free end 5a; in other words, the ablation head 3, when in use, is positioned between the outer tubular body 4a and the positioning head 2 (see FIG. 2 or 11, 12, for example).

In general, the ablation head 3 comprises a plurality of ablation elements or petals 3a.

In the embodiment illustrated, there are four ablation petals 3a, but there could also be two, three or more.

Figure 3:
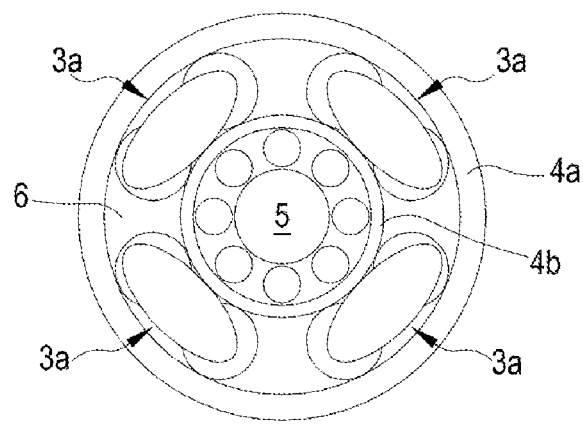
FIG. 3 illustrates a front view of the catheter of the invention in an insertion condition.
Figure 4:
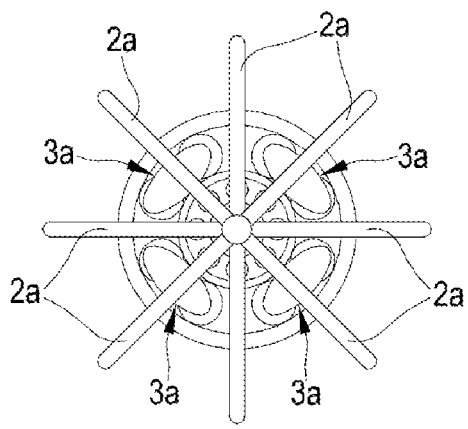
FIG. 4 illustrates a front view of the catheter of the invention in a positioning condition corresponding to that of FIG. 1.
Figure 5:
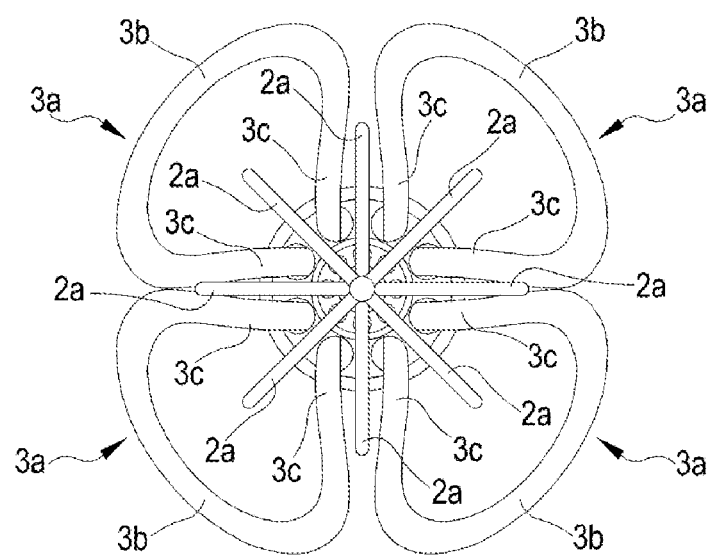
FIG. 5 illustrates a front view of the catheter of the invention in a functioning condition corresponding to that of FIG. 2.

A specific feature of the ablation elements 3a is that they can be moved, or rather extracted, from a rest position in which they are housed in the outer tubular body 4a (as in FIGS. 1, 3 and 4) to an operating position in which they protrude from the outer tubular body 4a extending and broadening out both radially and axially towards the positioning head (as in FIGS. 2, 5, 11-14).

The movement between the two positions, rest and operating, is effected thanks to a mechanical control positioned in the handpiece of the device and which allows the controlled and adjustable extraction of the ablation petals 3a.

In short, between the inner tubular body 4b and the outer tubular body 4a, there is at least one housing chamber 6, in which the petals 3a are positioned in a rest condition and from which they are extracted to be brought into an operating condition.

In some embodiments, a single housing chamber is envisaged for each petal 3a, whereas in other embodiments, such as that illustrated, there is only one chamber 6, which in a sectional and front view, is substantially in the form of a circular crown, as it is formed between the outer 4a and inner 4b tubular bodies.

This allows the elements 3a, when in a rest condition, to be kept withdrawn inside the chamber 6 during the positioning phase of the catheter (see FIGS. 1, 3 and 4), without creating an obstacle during the passage of the catheter inside the patient's veins, and to be extracted from the chamber 6 only when the catheter 1 is positioned.

At least one, preferably all, of the ablation elements 3a comprise a continuous (clearly visible in FIG. 5)—or distributed—ablation electrode 3b which extends without interruption over a circumferential portion, preferably peripheral, of each petal 3a, substantially along an arc of circumference having a longitudinal axis of the rod-like guiding element 5, as center.

In other words, the electrode 3b occupies the whole of the external body of the petal 3a, as far as the folded portions with a larger curvature radius which connect it with two side portions 3c of the petal 3a, each connected to an end of the ablation electrode (3b).

Characteristically, the side portions 3c and the ablation electrode 3b are integral with each other, produced with the same folded metallic conductor, to which further reference will be made hereunder.

In short, the petal is composed of a single, folded, solid electric conductor (wire or lamina), of which the circumferential part 3b forms the actual electrode and the side parts 3c form side portions of the petal which preferably do not contribute to the ablation process, even if traversed by an electric current.

This effect is obtained, for example, by coating the side portions 3c with a layer of electrically insulating material, preferably a paint (not illustrated in the figures).

Each ablation petal 3a is separate and distinct from another ablation petal of the ablation head and all the ablation petals 3a of the head are connected separately to a separate electric energy generator to cause a radiofrequency ablation under a powered condition of the ablation electrode 3b.

In this way, the quantity of energy to be supplied in relation to the desired result, can be regulated with extreme precision.

The electrically conductive material forming the ablation petal 3a is preferably composed of a shape-memory metallic conductor, even more preferably a Nitinol wire, a material which is known per sé for biomedical use; it should be noted that, in general, other metals/metal alloys suitable for the purpose, can also be selected.

As it is fundamental for the safety and success of the procedure to obtain a clear, continuous, ablation line, without causing surface necrosis and damage to the tissue, ideal conditions for enabling this can be obtained when the petals are of Nitinol, each produced with a single wire having a circular section with a diameter D and with the following ratio between the diameter D and the length L of the active part (circumferential part of the petal, or electrode)

D/L ranging from 0.015 to 0.025, preferably equal to about 0.02.

The electrical and mechanical characteristics are therefore optimized in relation to the advantages discussed above.

It should also be noted that by joining (ideally) the ablation electrodes 3b, they substantially develop along the same circumference, having the axis of the guiding element 5 as centre; only small arcs of this ideal circumference can remain unjoined (and therefore inactive in the ablation treatment); in this way, during a treatment, an important portion of a blood vessel can be ablated, leaving only small areas of tissue that do not receive direct treatment.

This can be obtained even more so thanks to the fact that, as the petals 3a are all produced with the same conductor and with the same dimensions, the elasticity is such that an optimal adherence of the petal to the surface has been observed (the petal under the action of the force against the tissue, becomes elastically deformed until it adheres perfected to the tissue itself, regardless of rhythmic movements of the same) obtaining optimum results in terms of ablation and also in preventing the formation of clots.

In this sense, thanks to the optimal adherence, a reduced overall quantity of energy can in fact be supplied with respect to cases of the known art, with a consequent lesser heating of the blood possibly in contact with the electrode; at the same time, there is also a lesser heating of the tissue, avoiding necrosis phenomena.

These small non-treated areas can be subsequently ablated by the surgeon, if necessary, for example by rotating the whole catheter 1 on itself or, more advantageously, only the petals 3a, keeping the positioning head 2 fixed.

It should be pointed out that the small angular extension of the arcs in which the ablation electrode 3b is not active, ensures that the surface treated by each activation of the ablation petals 3a, is high, much higher than the known radiofrequency catheters with an ablation tip described above.

This allows a more rapid treatment of the patient, with the advantages indicated above.

Referring again to the side portions 3c, with reference to FIG. 2, it can be noted that, in the preferred embodiment illustrated, these do not develop exactly according to a perpendicular axis to that of the guiding element 5 (more specifically, they do not lie on the plane on which the axis of the guiding element 5 is normal): the side portions 3c are in fact slightly tilted (in a side view) towards the free end 5a of the guiding element 5, specifically forming a petal.

The side portions 3c therefore preferably develop, at least partly, along the generatrices of a cone (or truncated cone, depending on the cases) having as axis the longitudinal axis of the guiding element 5.

In this way, also due to the intrinsic elasticity of the elements 3a (whether they be metal laminates or wires), when the ablation segment 3b is resting on the tissue to be ablated, they are able to dampen, by bending, small oscillations or physiological movements (of both the tissue and surgeon's hand), always keeping the ablation electrode 3b in contact with the tissue itself, guaranteeing a reliable contact and a consequent effective treatment, with the advantages discussed above.

For each petal 3a, one of the side portions 3c is preferably fixed to the outer tubular body, whereas the other side portion extends (or is connected) as far as the handpiece, where it is connected to the mechanical activation elements or to the specific generator for this.

Each petal, in addition to being individually activated, can also be individually extracted from the tubular body 4a in which it is housed in a non-operating condition.

Figure 17:
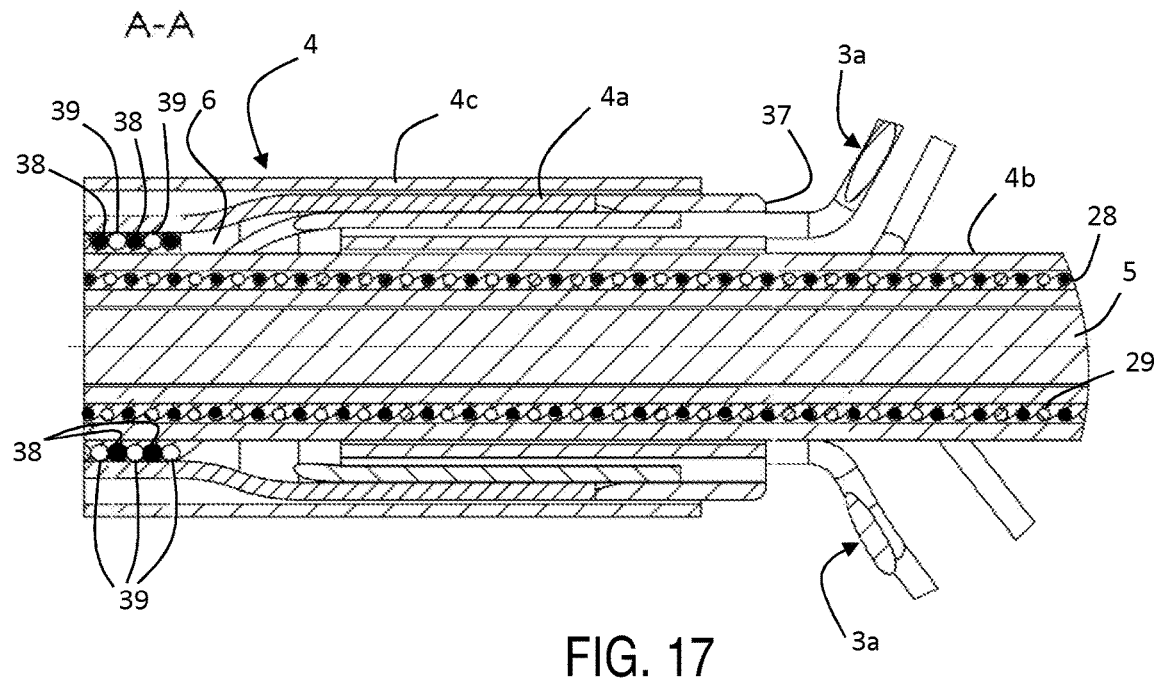
FIG. 17 illustrates a section along the plane AA of FIG. 11.
Figure 18:
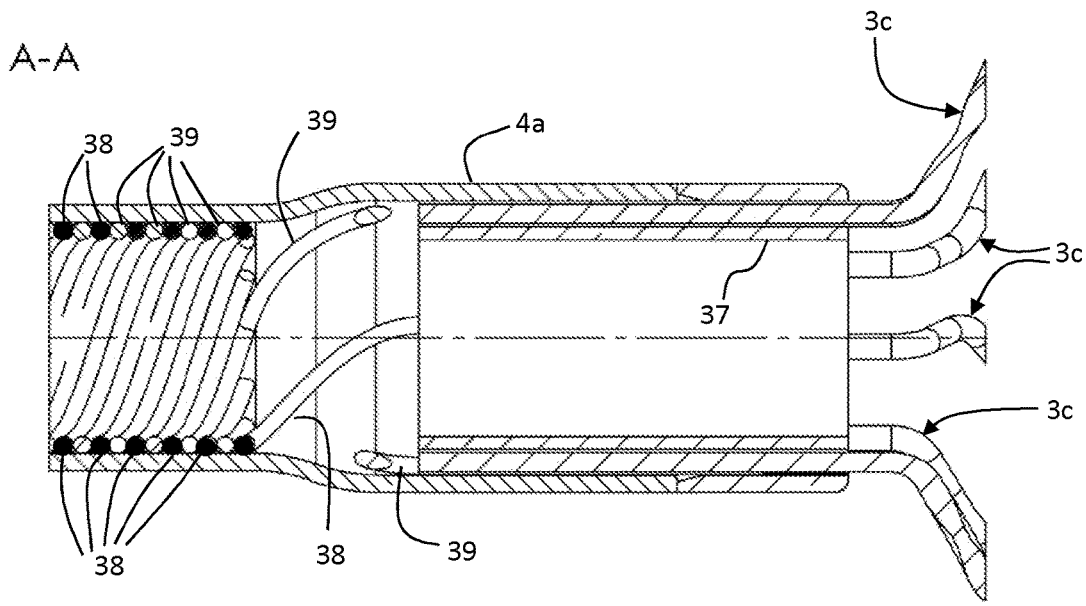
FIGS. 18 and 19 illustrate sections along the planes AA and BB of FIG. 13.
Figure 19:
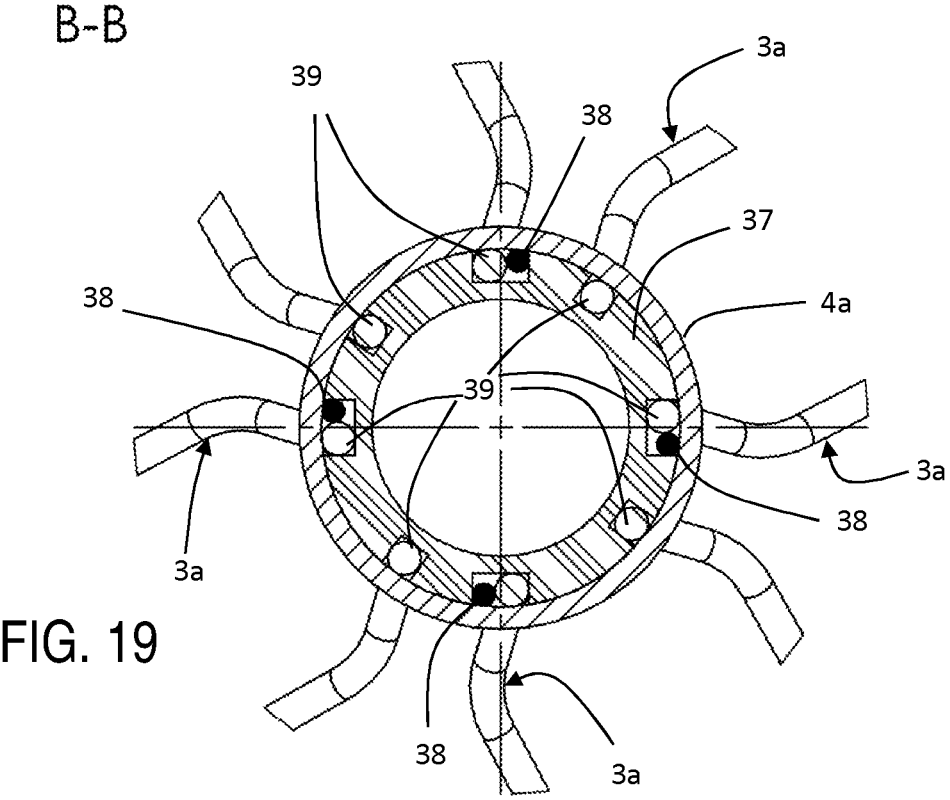
Figure 21:
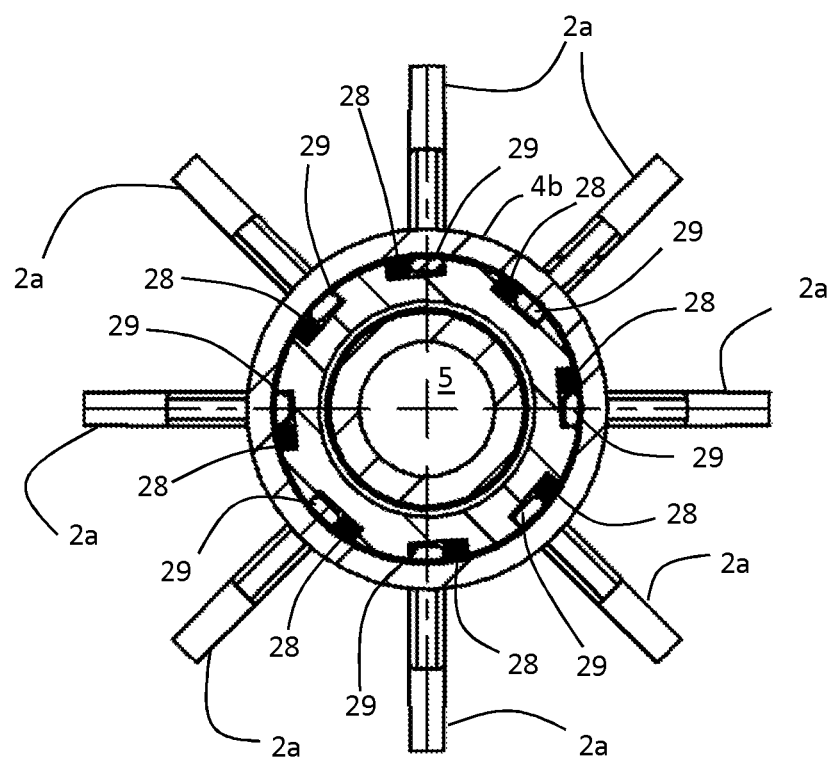
FIGS. 20 and 21 illustrate sections along the planes AA, BB and CC of FIG. 15.
Figure 20:
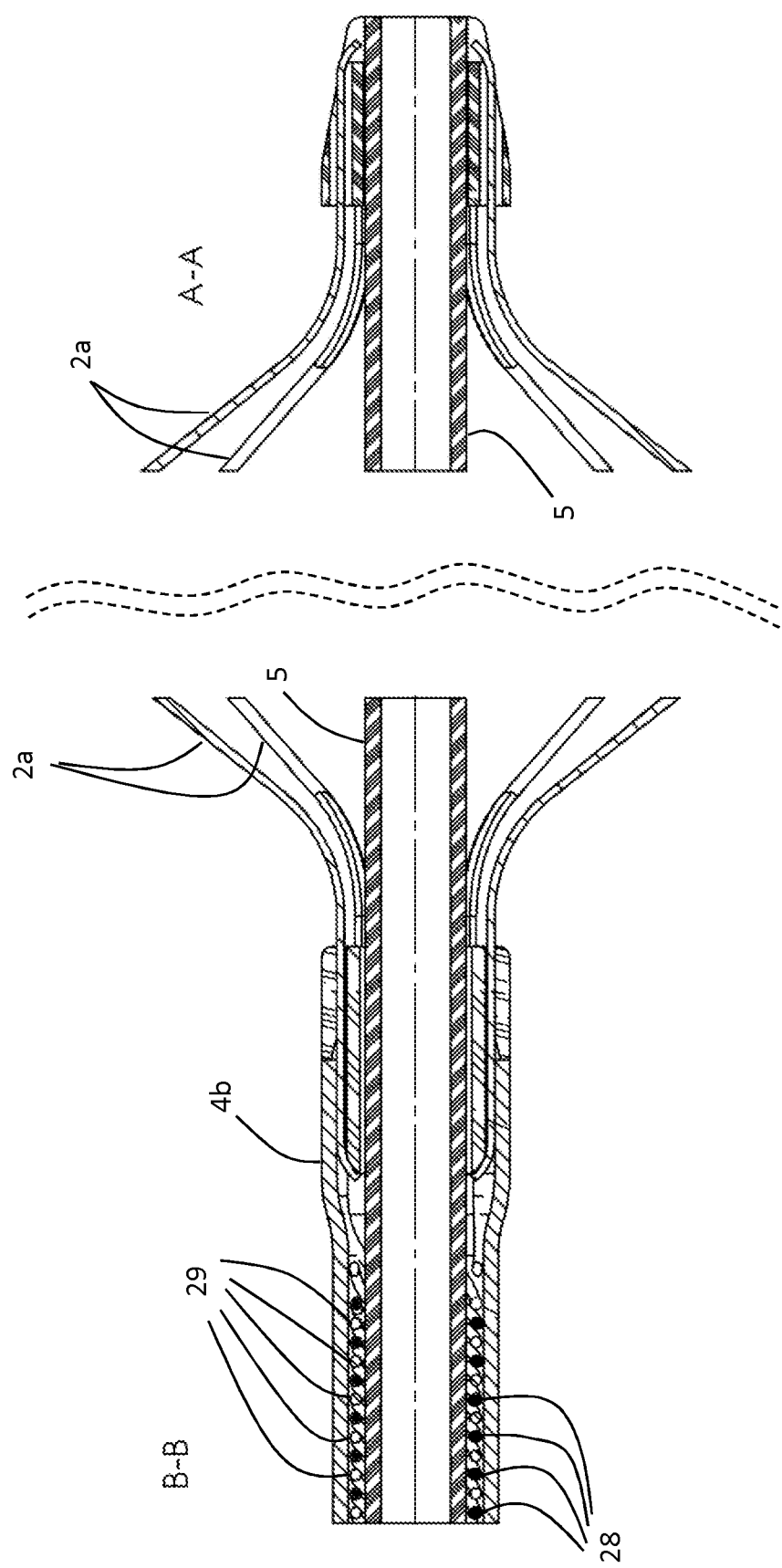

For this purpose, as can be seen in FIGS. 17, 18, 19, the side portion 3c of each petal is both mechanically and electrically connected to a specific conductor 39.

In the preferred embodiment of FIGS. 17, 18, the conductor 39 is integral with the petal 3a, as it is produced with the same Nitinol wire, with the same diameter.

In this preferred embodiment, only one side portion 3c of each petal extends as far as the handpiece, the other portion being fixed in correspondence with the terminal end of the body 4a, for example a terminal bush; the bush 37 therefore preferably slidingly houses a side portion of each petal 3c, whereas the other terminal portion of the same petal is fixed to the bush 37 itself.

In the preferred example of FIGS. 11-21, there are four petals 3a, therefore eight side portions 3c and consequently there will be four conductors 39 which extend as far as the handpiece.

It should be noted that in this preferred embodiment, the conductors 39 of each petal substantially extend as far as the handpiece housed inside the body 4a, in the space between this and the body 4b.

In this route that passes from the petals to the handpiece, the conductors 39 are spirally wound in said space between the bodies 4a and 4b.

Each conductor 39 is electrically isolated from the other so that the powering of one of these does not cause the powering of those nearby.

Again, with brief reference to the ablation electrodes 3b, in a particularly advantageous embodiment, they can be selectively activated: in short, each segment 3b and/or each element 3a is connected to a power source separately from the others and can be activated individually; for this purpose, the ablation apparatus of the invention comprises a number of radiofrequency electric energy generators equal to that of the petals, which are connected separated and individually to each generator by means of the conductors 39.

Each electrode 3b and/or each petal 3a is therefore connected individually to and can be powered individually by an electric energy source (preferably a radiofrequency generator).

The surgeon can therefore choose which electrodes 3b and/or petals 3a to activate depending on the treatment conditions, and can also repeat it only in correspondence with areas that have not been sufficiently treated and/or avoid activating areas of risk for the patient.

In a particularly advanced embodiment, each petal 3a can be advantageously moved individually (with respect to the others) between the rest condition and the, extracted, operating condition.

This allows the surgeon to extract only the ablation petals 3a that are necessary, for example when the dimensions/ forms of the tissue to be ablated have physiological features that make it advisable.

The ablation petals 3a are optionally rotatingly associated with the telescopic body 4 so that they can be rotated without causing the body 4 and/or the positioning head 2 to also rotate; this is obtained, for example in the case of the embodiment of FIGS. 11-21, making the terminal bush 37 (provided with seats in which the conductors 39 pass axially before being connected to the portions 3c) rotate freely with respect to the body 4a.

The petals 3a are preferably controlled by the handpiece of the device, by means of a mechanical, or electric or pneumatic control.

This allows a high flexibility of use to be obtained together with a considerable precision: when the surgeon has positioned the catheter 1 in an operating position, he keeps it in the correct position thanks to the positioning head 2 (to which further reference will be made hereunder), and can proceed with treating the various parts of tissue, extracting, rotating and activating the petals 3a alone, without having to repeat the positioning phase each time.

This contributes, inter alia, to making the treatment even more rapid, with the advantages indicated above.

According to an optional and advantageous characteristic, also regardless of the other features of the invention, at least one—preferably a plurality—of additional conductors 38 is envisaged, partly housed in the telescopic tubular body 4, shown in the preferred embodiment of FIGS. 11-21.

The additional conductors 38 are also housed in the body 4a, in the space between this and the body 4b, adjacent to the conductors 39, in particular spirally arranged and interspersed with the latter.

Said additional conductors 38 are not in electric contact with the petals 3a and serve to reduce the eddy currents and allow a better control of the energy supplied to each petal during the operating phase of the catheter.

These advantages are more strongly felt when ablation petals such as those described above are used, which are connected independently to the generators; in this way, eddy currents can be avoided, which could make the treatment less precise.

This advantage is offered when the ablation apparatus comprises discretized electrodes and also when the electrodes are continuous, as in the catheter described above.

Eddy currents are generated on the electrodes that are not fed due to those that are being fed at the same time by the respective generator and also cause the powering of the electrodes which, on the other hand, should not be fed.

The additional conductors 39 are preferably completely contained in the telescopic tubular body 4 and exit from this only on the side of the handpiece.

Each additional conductor is preferably "U"-folded inside the body, with the two free ends exiting from the proximal side and the folded part which extends into the tubular body as far as its end; alternatively and preferably, all or only part of the additional conductors can be electrically connected to each other.

The additional conductors 39 are preferably copper wires.

When the supply conductors of the electrodes are spirally wound in the body 4, the additional conductors 38 are interposed between them, so that each supply conductor 39 of a petal is adjacent, on the two opposite sides, to two branches of the same—or different—additional conductors 38.

This arrangement, shown in detail in FIGS. 17, 18, 19 allows the phenomenon of eddy currents described above to be completely or almost completely eliminated, so that the ablation treatment can be controlled with extreme accuracy.

Finally, according to another optional and advantageous feature, the ablation head 3 comprises at least one contact sensor, capable of measuring the contact with the surface to be treated, effecting the treatment with greater precision.

In particular, in one embodiment, said contact sensor is a capacitive sensor, which indirectly measures the percentage of the electrode 3b which is in contact with the tissue.

If the ablation is obtained by means of RadioFrequency (RF), for example, the same electrode 3b acts as electrode of the capacitive sensor: by passing a control current, it is in fact possible to reveal whether the same is or is not in contact with the tissue.

With respect now to the positioning head 2, this comprises a plurality of extractable positioning arms 2a.

Said arms 2c pass from a rest position, in which they are housed in the inner tubular body 4b, to an extracted, operating, position, in which they protrude radially from this.

Also in this case, analogously to the ablation head 3, the extractable positioning arms 2a remain withdrawn during the insertion phase of the catheter into the vein, until this has reached the area to be treated, so as not to represent an obstacle during this phase, and they are extracted to maintain the position reached, buffered against the walls of the vein/artery to be treated.

In particular, the extractable arms 2a are preferably housed between the inner tubular body 4b and the rod-like guiding element 5.

The extractable arms 2a form a kind of positioning cage, destined for abutting inside the vein, so as to keep the ablation head correctly in position in correspondence with the ostium of the vein itself.

In the embodiment illustrated, there are advantageously eight extractable positioning arms 2a, but, more generically, there could be two, three, four or more.

Also in this case, the extractable positioning arms 2a are controlled, in the extraction/re-insertion movement (from the rest position to the operating position and vice versa) by means of a mechanical system situated in the handpiece of the device and which allows the controlled and adjustable exiting of the extractable elements 2a.

In other embodiments, the positioning head is an inflatable body (not shown) which is expanded from the rest position to the operating position, like a balloon.

Also in this case, the inflatable body is preferably housed, under rest conditions, inside the tubular body 4.

The advantages of using a positioning head 2 provided with arms 2a, with respect to the inflatable body, are, first of all linked to the fact that the former solution does not block the passage of blood in the vein, as would be the case, on the contrary, with a balloon inflated internally (possibly causing clots or pulmonary hypertension phenomena).

The inflatable body, moreover, has the advantage of being able to be filled with radio-opaque fluid for a better and more precise visualization.

According to a particularly advantageous characteristic, regardless of its practical embodiment, the positioning head 2 comprises at least one sensor capable of revealing electric potentials in the tissue, consequently allowing the completeness of the ablation effected, to be revealed.

This sensor, can be produced in various ways, according to the case.

It can, for example, be an electrode applied to the arms 2a or to the inflatable body.

Alternatively, when the positioning head 2 comprises metal arms 2a, these, in practice, form the electrode for the detection, thanks to which the electric potentials of the vein are revealed and the isolation of the vein is verified during and at the end of the treatment.

As far as the positioning head 2 described above, is concerned, it is interesting to note how this comprises, in both the embodiment described above and also in its variants 2", 2'", 2°, 2*, 2^ which will be briefly described hereunder, at least one extractable positioning arm 2a (and 2a",2a'", 2a°,2a*,2a^ in the variants described hereunder) that can be moved between a rest position, in which it adheres to the rod-like guiding element 5 and is housed in the body 4 of the catheter, and an enlarged operating position, in which it protrudes from the rod-like guiding element 5, broadening out in a radial direction.

The guiding rod-like element 5 slides in the inner tubular body 4b; the positioning head 2, 2", 2'", 2°, 2*, 2^, under rest conditions, has such dimensions that it can be inserted in the inner tubular body 4b.

The catheter 1 can then be inserted into the vein so as to occupy a minimum space and there are no protrusions which could obstruct its passage in the patient's body, subsequently, when the catheter 1 is in the area to be treated, the rod-like element 5 is extracted from the inner tubular body 4b and, when the catheter has reached a correct position, in which it must be fixed, the positioning head 2, 2", 2'", 2°, 2*, 2^, is enlarged or, rather, its arms 2a, 2a",2a'",2a°,2a*,2a^ are enlarged, which pass from a rest position to an enlarged position and can be abutted against the surrounding tissues, so as to keep the catheter 1 in position.

The synergy of advantages deriving from the combined use of an ablation head 3 and a positioning head 2, according to the invention, are therefore evident.

With respect to the description of the alternative forms of the positioning head, reference should be made to FIGS. 6 to 10.

In the figures, the catheter 1 is shown with the ablation head in a rest condition and, for the sake of clarity, only the positioning head is illustrated.

In this respect, it should be noted that, in order to avoid encumbering the present description, no further mention is made hereunder of the elements and characteristics in common with the head 2 and arms 2a, already presented above; it should also be noted that the same parts illustrated in the previous figures are indicated with the same reference numbers.

Figure 6:
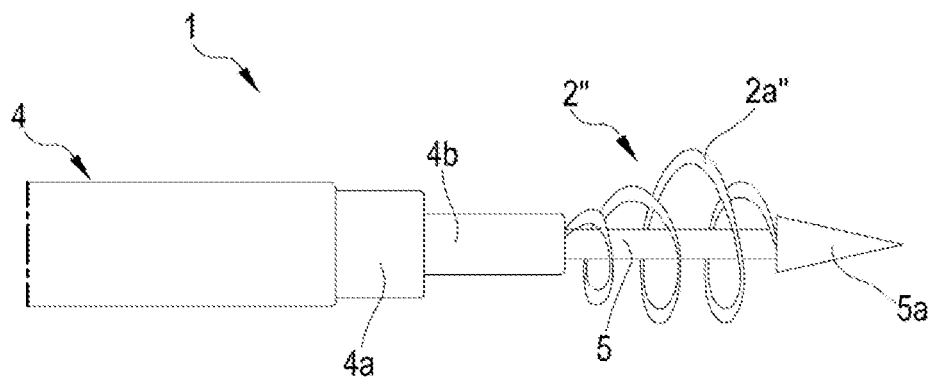
FIGS. 6-10 illustrate side views of variants of a detail of the catheter of the invention.
Figure 7:
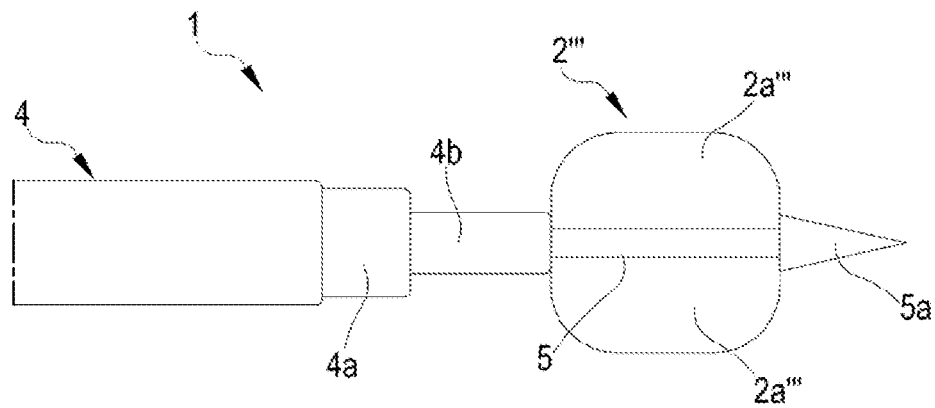
Figure 8:
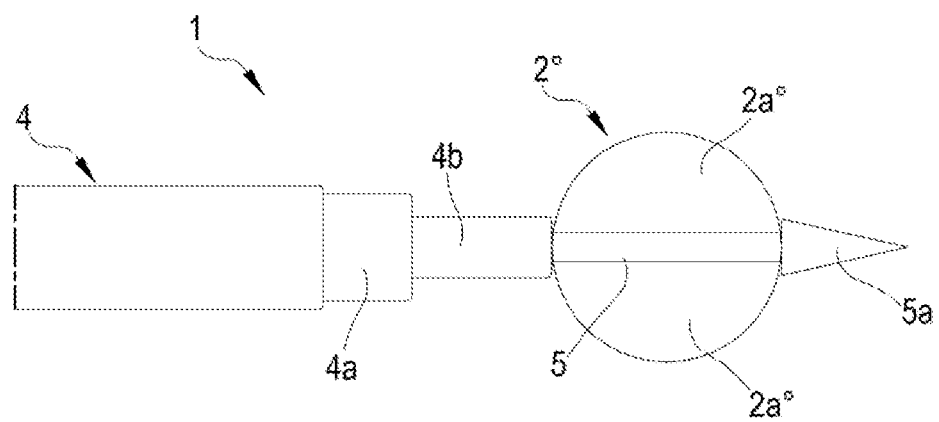

FIG. 6 shows a positioning head 2" in an enlarged condition, which comprises only one arm 2a", in the form of a spiral which develops around the rod-like element 5.

When in an extracted condition, the arm 2a" rests with its coils on the tissue, helping to keep the catheter 1 in position.

Figure 9:
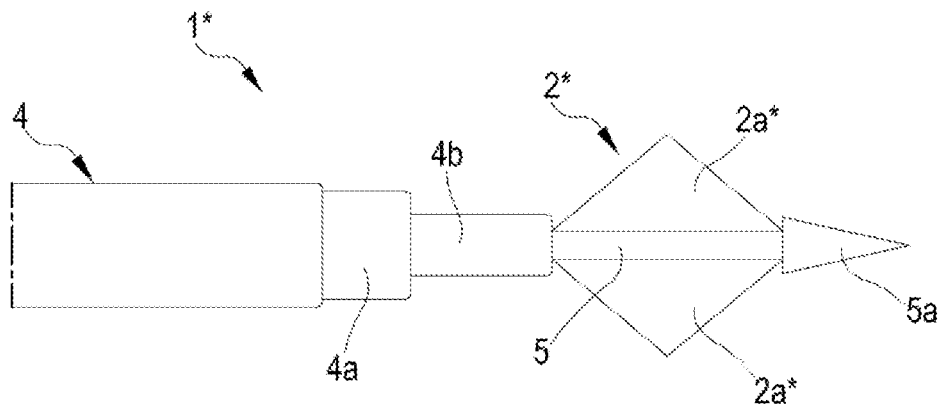
Figure 10:
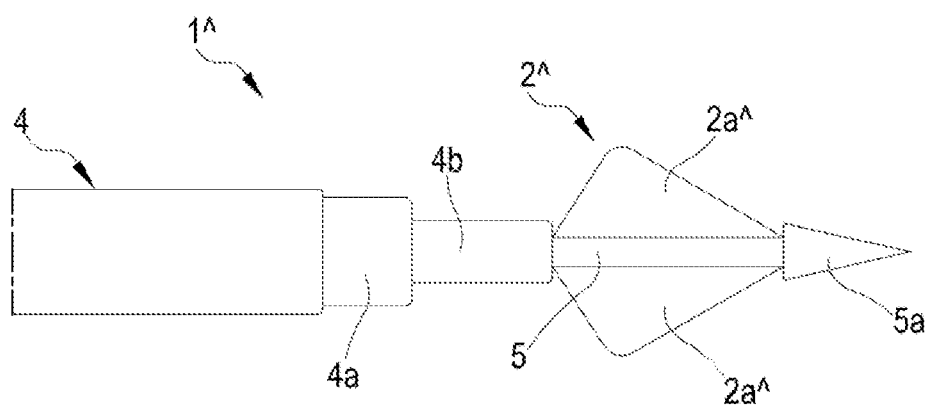

FIGS. 7, 8, 9 and 10 show, in an enlarged condition, the positioning heads 2''', 2°, 2* and 2^ each comprising arms 2a''', 2a°, 2a* and 2a^ which extend according to different geometries around the rod-like element 5: the arms 2a''', in an extended condition, each form a kind of rectangle (in a side view) with rounded edges, the arms 2a°, in an extended condition, each form a kind of semicircle (in a side view), the arms 2a*, in an extended condition, each form a kind of isosceles triangle (in a side view) as depicted by catheter 1* of FIG. 9, the arms 2a^, in an extended condition, each form a kind of semi-arrow (in a side view) with rounded edges as depicted by catheter 1^ of FIG. 10.

It should be noted, moreover, that each extractable arm 2a, 2a", 2a''', 2a°, 2a* and 2a^ is arched (even if it does not develop according an actual arc of circumference except for the arms 2a°) and extends substantially between said inner tubular body (4b) and said free end (5a) of said rod-like element (5).

Even if two arms are shown in the examples of these variants, three, four or more arms can be envisaged, similar to the arms 2a described above.

With reference to FIGS. 11-21, which show a preferred embodiment, it should be noted that, analogously to the conductors 39 of the petals, each arm 2a of the head 2 also extends into the body 4b as far as the handpiece by means of elongated spiral-shaped portions 29.

Each elongated portion is preferably integral with the respective arm 2a and is produced in the same material, preferably conductive such as Nitinol or similar.

Inside the body 4b, more specifically in the space between this and the guidewire 5, each elongated portion 29 is electrically isolated from the others, so that possible electric signals can be revealed (or transmitted) by the arms 2a independently of each other.

In the enclosed preferred embodiment, moreover, additional second conductors 28 are envisaged for the positioning head 2, with advantages similar to those described above for the first additional conductors 38 (relating to the eddy currents).

These additional conductors 28 develop on a helix having the same pitch and the same diameter with respect to the elongated portions 29, and are interspersed with the latter, so that each elongated portion 29 of an arm 2a is adjacent, at the two opposite sides, to two branches of the same—or different—additional conductor(s) 28.

In short, the effects relating to the reduction in the phenomena of eddy currents are thus reduced or even cancelled.

The additional conductors 28 are preferably made of copper, preferably shaped like U-folded wires inside the body 4b (or, alternatively, preferably all or part of them are electrically connected to each other), between this and the guidewire, analogously to the additional conductors 38 described above.

In the ablation apparatus, the above-mentioned additional dissipative conductors 28, 38 are preferably electrically connected to ground.

The objectives indicated above have therefore been achieved.

The invention claimed is:

1. A catheter for the ablation of tissues comprising:
a telescopic tubular body in turn comprising an external tubular body and an internal tubular body concentric with each other, and a rod-like guiding element at least partly housed in the internal tubular body with at least one free end protruding from the internal tubular body in correspondence with a distal end of the telescopic tubular body;
a positioning head and an ablation head in correspondence with the distal end of the telescopic tubular body, the positioning head being situated in the proximity of the free end of the rod-like guide, and the ablation head in the proximity of the positioning head, in a remote position with respect to the free end;
a control handpiece at a proximal end of the telescopic tubular body coupled with the guiding element, the ablation head, the positioning head and the telescopic tubular body;
wherein the ablation head comprises at least two ablation elements or petals that can be moved from a rest position in which they are housed in the external tubular body and an operating position in which they protrude from the external tubular body like a petal, each ablation element or petal extending and broadening out both radially and axially towards the positioning head;
each of the ablation elements or petals comprising:
a single, continuous ablation electrode which extends without interruption over a circumferential peripheral portion of each petal, substantially along an arc of circumference having a longitudinal axis of the rod-like guiding element as its center, the continuous ablation electrode occupying an entirety of the circumferential peripheral portion;
two side portions of the petal, each connected to an end of the ablation electrode, in correspondence with a respective curved section, wherein each of the two side portions do not contribute to ablation while allowing for traversal of electric current from an electric energy generator to the ablation electrode,
characterized in that the side portions and the ablation electrode are integral with each other, formed by means of the same folded metallic conductor,
each ablation petal being separate and distinct from another ablation petal of the ablation head, wherein the ablation petals are arranged in a non-overlapping manner relative to one another,
all the ablation petals of the ablation head being separately connected to a distinct electric energy generator to cause a radiofrequency ablation from respective ablation electrodes in a powered ablation electrode condition, and
wherein each ablation petal is produced with a single Nitinol wire having a diameter D along an entire length extending from at least a first side portion to a second side portion, including the circumferential peripheral portion therebetween, and wherein the circumferential peripheral portion of each ablation petal, positioned between a respective set of two side portions and along which the single continuous ablation electrode extends, has a linear length L, such that a ratio D/L ranges from 0.015 to 0.025, wherein D is the diameter of the wire from which the circumferential peripheral portion is formed and L is the linear length of the circumferential peripheral portion formed by the wire.

2. The catheter according to claim 1, wherein said ratio D/L is equal to about 0.02.

3. The catheter according to claim 1, wherein the two side portions of each petal are coated with an electrically insulating material.

4. The catheter according to claim 3, wherein the electrically insulating material is an insulating paint.

5. The catheter according to claim 1 comprising, for each petal, at least one conductor which extends as far as the handpiece for individually powering each petal, wherein said conductor extends inside the external tubular body, in the space between the external tubular body and the internal tubular body.

6. The catheter according to claim 5, wherein said conductor is arranged spirally.

7. The catheter according to claim 1 comprising, for each petal, at least a first additional conductor at least partly housed in the telescopic tubular body, and destined for preferably extending from the handpiece to the end of the external tubular body.

8. The catheter according to claim 7, wherein each first additional conductor develops spirally inside the external tubular body, and wherein said conductors alternate with at least one additional conductor, inside said external tubular body.

9. The catheter according to claim 1, wherein each petal can be moved individually with respect to the others between the rest condition and the extracted, operating condition.

10. The catheter according to claim 1, wherein the ablation petals are rotatably associated with the telescopic tubular body so that they are adapted to be rotated without causing the body and/or the positioning head to also rotate.

11. The catheter according to claim 1, wherein the positioning head comprises at least one extractable positioning arm, said extractable positioning arm being movable between a rest position, in which it is housed in the internal tubular body, and an extracted, operating position, in which it protrudes radially from the internal tubular body.

12. The catheter according to claim 11, wherein said at least one positioning arm is metallic and forms the detection electrode.

13. The catheter according to claim 12, wherein each of said at least one positioning arm is connected to at least one elongated portion which extends as far as the handpiece, housed in the internal tubular body.

14. The catheter according to claim 13, wherein second additional conductors are for the positioning head and are interspersed with said elongated portions.

15. The catheter according to claim 14, wherein the second additional conductors develop spirally.

16. The catheter according to claim 13, wherein the at least one elongated portion is spiral shaped.

17. The catheter according to claim 1, wherein the positioning head comprises at least one sensor adapted to reveal the completion of ablation by sensing the electrical potentials in the tissue.

18. An apparatus for the ablation of tissues comprising a catheter according to claim 1 and at least one electric energy generator for each petal of said catheter, electrically connected to said petal.

* * * * *